US00PP09938P

United States Patent [19]

Zaiger et al.

[11] Patent Number: Plant 9,938

[45] Date of Patent: Jul. 1, 1997

[54] PEACH TREE "SNOW DANCE"

[76] Inventors: Chris Floyd Zaiger, 929 Grimes Ave.; Leith Marie Gardner, 1207 Grimes Ave.; Gary Neil Zaiger, 1907 Elm Ave.; Grant Gene Zaiger, 4005 California Ave., all of Modesto, Calif. 95358

[21] Appl. No.: 620,555

[22] Filed: Mar. 25, 1996

[51] Int. Cl.[6] ..... A01H 5/00

[52] U.S. Cl. ..... Plt./42.1

[58] Field of Search ..... Plt./42.1

*Primary Examiner*—James R. Feyrer

[57] ABSTRACT

A new and distinct variety of peach, *Prunus persica,* tree; its novelty consists of the following unique combination of desirable features that are outstanding in a new variety:

1. Early maturity of large size fruit.
2. Fruit with good flavor and eating quality.
3. Heavy and regular production of fruit.
4. Fruit with a high degree of attractive red skin color.
5. Fruit with firm flesh, good handling and shipping quality.
6. The ability of the fruit to hold firm on the tree 4 to 5 days after maturity (shipping ripe).
7. Vigorous, upright growth habit.

1 Drawing Sheet

ORIGIN OF THE VARIETY

The new and distinct variety of peach tree was originated by us in our experimental orchard located near Modesto, Calif., as a first generation cross between two selected seedlings with field identification numbers 36EB85 and 5GE8. The female parent (36EB85), originated from an open pollinated seedling selection selected from a cross between May Grand Nectarine (U.S. Plant Pat. No. 2,794) with a peach of unknown parentage. The pollen parent (5GE8), originated as a selected seedling from a cross between Fayette Peach (non-patented) with Royal April Peach (U.S. Plant Pat. No. 3,411) which was then crossed with May Crest Peach (U.S. Plant Pat. No. 4,064). A large number of these first generation seedlings were grown and maintained under close observation by us, during which time we recognized the outstanding desirable characteristics described above and selected the present new variety for asexual reproduction and commercialization.

ASEXUAL REPRODUCTION OF THE VARIETY

The present new variety of peach tree was asexually reproduced by budding, as perform by us in our experimental orchard located near Modesto, Calif., and shows that all characteristics run true to the original tree and are established and transmitted in succeeding asexual propagations.

SUMMARY OF THE VARIETY

The new and distinct variety of peach tree is of large size, vigorous, upright growth and a productive and regular bearer of large, white flesh, clingstone fruit with good flavor and eating quality. The fruit is further characterized by having firm flesh, good handling and shipping quality, holding firm on the tree 4 to 5 days after maturity (shipping ripe) and having a high degree of attractive red skin color. In comparison to the white flesh, Sugar May Peach (U.S. Plant Pat. No. 8,034), the fruit of the new variety is approximately 13 days earlier in maturity.

DESCRIPTION OF THE PHOTOGRAPH

The accompanying color photographic illustration shows typical specimens of the fruit and foliage of the present new peach variety. The upper and lower surface of the leaves being shown, the exterior and a sectional view of a fruit divided in the suture plane to show flesh coloration, pit cavity and a stone remaining in place. The photograph was taken shortly after the fruit was picked at maturity (shipping ripe) and the colors are as nearly true as is reasonably possible in a color representation of this type.

DESCRIPTION OF THE VARIETY

The following is a botanical description of the present new peach tree, its flowers, foliage and fruit as based on observations of specimens grown near Modesto, Calif., with color terminology (except those in common terms) referenced to Reinhold Color Atlas by A. Kornerup and J. H. Wanscher.

Tree:
- *Size.*—Large.
- *Shape.*—Usually pruned to vase shape.
- *Vigor.*—Vigorous.
- *Density.*—Medium dense.
- *Form.*—Upright.
- *Productivity.*—Productive.
- *Bearer.*—Regular.

Trunk:
- *Size.*—Medium to large.
- *Texture.*—Medium shaggy.
- *Color.*—Brown to grayish brown (5-E-4) to (5-F-4).

Branches:
- *Size.*—Medium.
- *Texture.*—Smooth to medium rough, varies with age of growth.
- *Lenticels.*—Medium number. Large size.
- *Color.*—Light brown to brown (5-E-6) to (5-D-6).

Leaves:
- *Size.*—Large. Average length — 6". Average width — 1½".
- *Form.*—Lanceolate, pointed.
- *Margin.*—Crenate.
- *Texture.*—Relatively smooth.
- *Thickness.*—Medium.
- *Petiole.*—Medium length. Medium thickness.
- *Glands.*—Reniform. Number varies from 1 to 3. Average number 2. Medium size. Positioned on base of leaf blade and upper portion of petiole.

*Color.*—Upper surface — green to dark green (27-D-6) to (27-F-6). Lower surface — dull green to grayish green (27-D-3) to (27-E-3).

Flower buds:

*Size.*—Medium to large.

*Length.*—Medium.

*Form.*—Plump.

Flowers:

*Size.*—Large, showy.

*Blooming period.*—Mar. 2, 1994 to Mar. 7, 1994. Varies slightly with climatic conditions.

*Pollen.*—Present, self-fertile.

*Color.*—Pink.

Fruit:

*Maturity when described.*—Firm ripe.

*Date of first picking.*—May 21, 1994.

*Date of last picking.*—May 26, 1994.

*Size.*—Large. Average diameter axially 2¾". Average transversely in suture plane 2⅞".

*Form.*—Globose, nearly rounded.

*Suture.*—Shallow, extends from base to apex.

*Ventral surface.*—Usually rounded.

*Cavity.*—Rounded, slightly elongated in suture plane. Average depth — ½". Average breadth — ¾".

*Base.*—Retuse.

*Apex.*—Nearly rounded, varies from round to slight apical point.

Flesh:

*Ripens.*—Evenly.

*Texture.*—Firm.

*Fibers.*—Few, small, tender.

*Juice.*—Moderate.

*Flavor.*—Good, mild, sub-acid, sweet.

*Eating quality.*—Good.

*Amygdalin.*—Undetected.

*Color.*—White to yellowish white (1-A-1) to (1-A-2). Pit cavity — pale yellow to grayish yellow (1-A-3) to (1-B-5).

Skin:

*Thickness.*—Medium.

*Texture.*—Medium, tenacious to the flesh.

*Tendency to crack.*—None.

*Down.*—Moderate amount. Short in length.

*Color.*—White to yellowish white ground color (3-A-2) to (3-A-3). Nearly overspread with red to madder red (10-B-8) to (10-D-8).

Stone:

*Type.*—Clingstone.

*Size.*—Medium to large. Average length — 1⅜". Average width — 1 1/16". Average thickness — ½".

*Form.*—Obovate.

*Base.*—Usually straight, varies from straight to rounded.

*Apex.*—Varies from rounded to acuminate.

*Sides.*—Equal to unequal.

*Surface.*—Irregularly furrowed toward apex, pitted toward base, pit cavities vary from round to elongated.

*Tendency to split.*—Very slight.

*Color.*—Tan to light brown (6-B-3) to (6-C-4).

Use: Dessert.

*Market.*—Local and long distance.

Keeping quality: Good.

Shipping quality: Good.

The present new variety of peach tree, its flowers, foliage and fruit may vary in slight detail due to climate, soil conditions and cultural practices under which the variety may be grown; the present description is that of the variety grown under the ecological conditions prevailing near Modesto, Calif.

I claim:

1. A new and distinct variety of peach tree, substantially as illustrated and described, characterized by its large size, vigorous, upright growth and being a productive and regular bearer of large, firm, white flesh, clingstone fruit with a mild, sub-acid, sweet flavor with good eating quality; the fruit is further characterized by having good handling and shipping quality, holding firm on the tree 4 to 5 days after maturity and, in comparison to the white flesh Sugar May Peach (U.S. Plant Pat. No. 8,034), the fruit is approximately 13 days earlier in maturity.

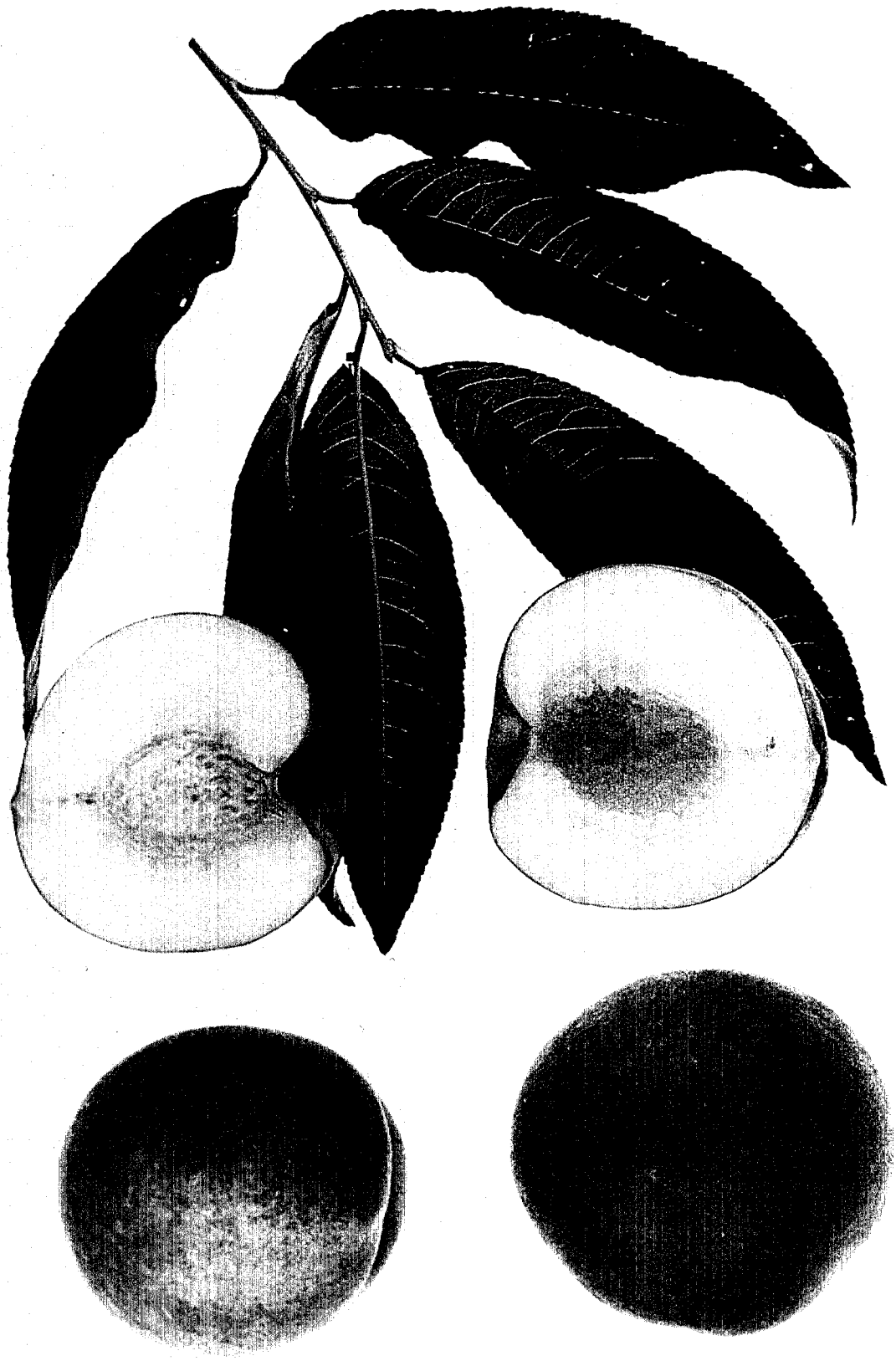

* * * * *